Figure 1:
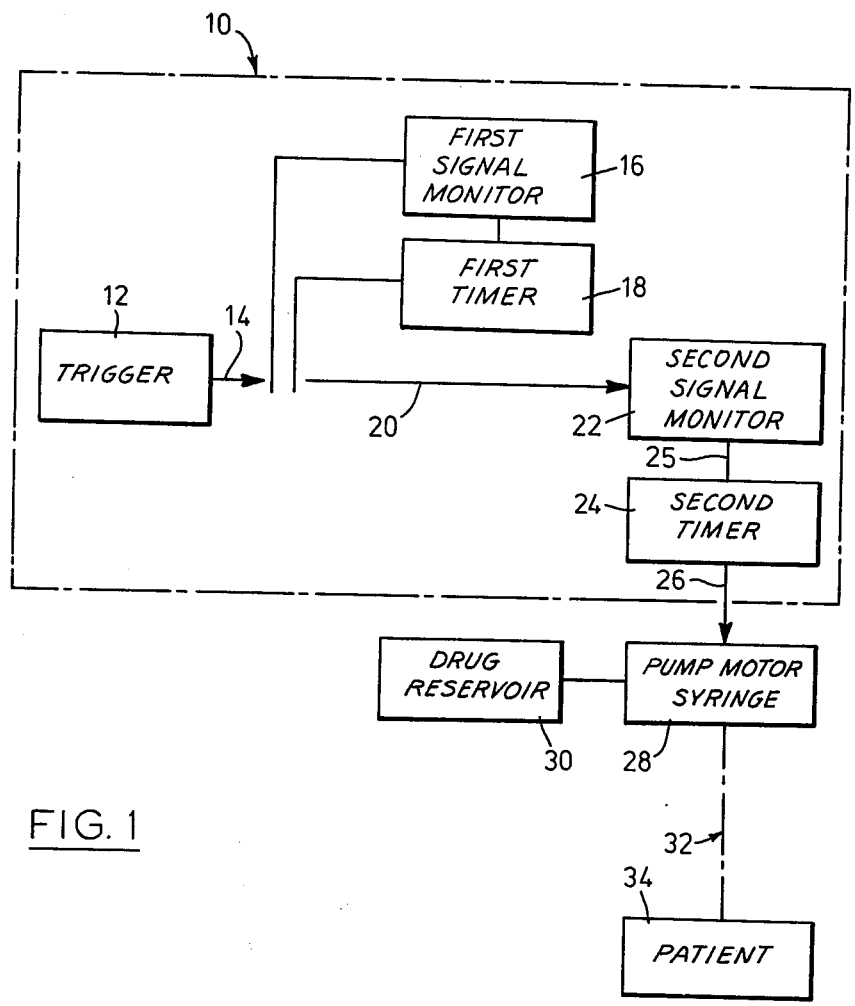

United States Patent [19]
Keeri-Szanto

[11] 4,275,727
[45] Jun. 30, 1981

[54] DEVICE FOR MONITORING AND CONTROLLING SELF-ADMINISTERED INTRAVENOUS DRUG DOSAGE

[76] Inventor: Michael Keeri-Szanto, 10 Beechwood Place, Apt. 612, London, Ont. N6C 1H7, Canada

[21] Appl. No.: 109,928

[22] Filed: Jan. 7, 1980

[51] Int. Cl.³ .............................................. A61M 5/00
[52] U.S. Cl. ...................... 128/214 E; 128/DIG. 13; 222/14
[58] Field of Search ............... 128/214 E, 214 R, 213, 128/DIG. 13; 222/14–22

[56] References Cited
U.S. PATENT DOCUMENTS

| | | | |
|---|---|---|---|
| 3,871,361 | 3/1975 | Kamen | 128/214 E X |
| 4,078,562 | 3/1978 | Friedman | 128/214 F X |
| 4,217,993 | 8/1980 | Jess | 128/214 E |

Primary Examiner—Stephen C. Pellegrino
Attorney, Agent, or Firm—Fetherstonhaugh & Co.

[57] ABSTRACT

A device for monitoring and controlling the operation of a motorized syringe to dispense a predetermined drug dosage comprises, according to one aspect of this invention, a combination of a trigger, a first signal monitor, a first timer, a second signal monitor and a second timer. The trigger is operable by the patient to initiate a demand signal indicative of a demand for an individual drug dose. The first signal monitor serves to record the total number of occasions on which a demand signal is initiated by operation of the trigger. The first timer receives the demand signal and selectively rejects the demand signal or emits the demand signal as an inject signal. The second signal monitor records the total number of occasions on which the first timer emits a demand signal. The second timer receives the inject signal and is operable upon receipt of the inject signal to activate a motorized syringe for a preselected time period to dispense a predetermined individual dose of drug.

2 Claims, 1 Drawing Figure

DEVICE FOR MONITORING AND CONTROLLING SELF-ADMINISTERED INTRAVENOUS DRUG DOSAGE

This invention relates to a device for monitoring and controlling self-administration of intravenous drug dosages.

PRIOR ART

Several instruments have been developed for the purposes of permitting a patient to control the rate of administration of drug dosages by an intravenous injection system. Motorized syringes capable of injecting a predetermined drug dosage in response to the receipt of an electrical signal are known. Examples of such motorized syringes are those sold under the trade name CARDIF PALLITOR and manufactured by Pye Electronics Limited.

In previously known devices for monitoring and controlling the operation of a motorized syringe, a trigger is provided which the patient can operate to generate a demand signal and a timer is provided for receiving the demand signal and selectively rejecting the demand signal or passing the demand signal as an inject signal to the motorized syringe and a single counter is provided. In one such prior device the counter counts the total number of occasions on which the trigger is activated. In another device the single counter counts the total number of occasions on which the timer passes the demand signal as an inject signal.

Generally it has been the practice to monitor the total number of inject signals as this serves to give the physician an indication of the total amount of drug which has been administered to the patient.

In order to control the level of pain which a patient experiences, it is necessary to maintain a certain drug level in the patient's blood. When drugs are administered by a physician or a nurse, it is necessary to maintain a dosing interval of the order of three to four hours. As a result of this practice, the initial blood level will be high and will decline progressively over the balance of the dosing interval. Thus, the patient initially receives an overdose of the drug which will decline and become an underdose toward the end of the dosing interval. It is well known that there are two techniques by which the high swing in blood level concentration may be reduced. One method is to employ drugs which have a long half-life and the other is to reduce the individual dosages and to shorten the dosing intervals. The use of analgesics which have a long half-life, such as morphine, makes it essential that the correct individual dosage for a particular patient be accurately determined because the patient's metabolism will require several hours to correct any such errors. In the alternative, where the dosage interval is to be shortened in order to reduce the blood level concentration swings, it is necessary to employ a machine which permits self-administration of drug dosages.

The previously known machines used for the self-administration of drug dosages permit a reduction in the size of the individual dose and a shortening of the dosing intervals. The effectiveness of the dosing strategy is, however, determined by the physician as a result of consultations with the patient. There are many circumstances under which a physician is unable to communicate with a patient in order to obtain an indication of the effectiveness of the dosing strategy. Under these circumstances it is very difficult for the physician to determine the effectiveness of the dosing strategy.

By providing a machine constructed in accordance with the present invention which provides an indication of the number of demand signals generated by the patient when he activates the trigger mechanism and the number of the successful inject signals, the physician is able to determine the effectiveness of the dosing strategy without having to question the patient directly. This is particularly true when an underdose condition exists. An underdose will be reflected in the two counters by a larger demand than dosage delivery. When an underdose condition is determined by reference to the monitors, it is possible for the physician to adjust the machine to deliver a larger individual dose or to permit a shorter dosing interval. Thus, it will be seen that the machine of the present invention will extend the range over which the adequacy of a dosing strategy can be verified.

According to one aspect of the present invention, a device for monitoring and controlling the self-administration of intravenous drug dosages administered by a motorized syringe comprises a trigger operable by a patient to initiate an electrical demand signal indicative of a demand for a drug dosage, a first signal monitor adapted to record the total number of occasions on which a demand signal is initiated at the trigger, a first timer for receiving the demand signal and selectively rejecting the demand signal or passing the demand signal as an inject signal to the syringe to activate the syringe, a second signal monitor adapted to record the total number of occasions on which an inject signal passes the first timer, and a second timer for receiving the inject signal which passes from the second signal monitor to activate the motorized syringe for a preselected time period.

The apparatus of the present invention will be more clearly understood after reference to the following detailed specification read in conjunction with the drawings wherein, FIG. 1 is a diagrammatic representation of a device for monitoring and controlling self-administration of intravenous drug dosages.

In FIG. 1 of the drawings, the reference numeral 10 refers generally to a device constructed in accordance with an embodiment of the present invention. The device includes a trigger mechanism 12 which is adapted to be operated by the patient to generate an electrical demand signal in the line 14. A demand signal counter or monitor 16 counts and records the total number of demand signals initiated by the patient. A timer 18 receives the demand signal and selectively rejects the demand signal or passes the demand signal as an inject signal to the line 20. A second monitor 22 records and counts the number of inject signals which pass along the line 20. The inject signal is transmitted along a line 25 to a second timer 24 which controls the operation of a pump motor 28 by completing the driving circuit of the motor for a preselected time period. The electrically driven pump motor 28 dispenses the required individual drug dosage from the reservoir 30 to an intravenous tubing 32 which leads to the patient 34.

Initially the first timer 18 is pre-set by the physician to provide a predetermined minimum dosing interval which will ensure that the patient cannot receive more than a predetermined maximum drug dosage within a predetermined time interval. The timer is preferably adapted to control the dosage interval within the range of 0 to 30 minutes. The individual dose is regulated by the duration of the setting of the second timer 24 which preferably has an operational range from 0 to 30 seconds.

In use, the first and second timers 18 and 24 are preset as previously indicated to provide a predetermined dosing interval and the individual dose which is expected to meet the patient's needs. The reservoir 30 is connected through the pump 28 to the intravenous tubing 32 which leads to the patient 34. The patient is given control of the trigger 12. Whenever the patient requires a drug dosage, he activates the trigger 12 which generates a demand signal in the line 14. The counter 16 counts and records the operation of the trigger 12 and the timer 18 will pass the first signal which it receives as an inject signal to the line 20. The inject signal in the line 20 is counted and recorded by the counter 22 and is passes to the timer 24 as an inject signal. The timer 24 then activates the pump motor 28 which operates for the period of time controlled by the timer 24 to dispense the required dosage.

If the patient activates the trigger 12 before the expiry of the dosing interval pre-set in the first timer 18, the demand signal which is generated will be counted by the first or attempt counter 16 and rejected by the timer 18. Repeated demand signals generated by the patient activating the trigger 12 before the expiry of the dosage interval will be counted and recorded by the attempt counter 16 but will not pass to the injector syringe until after the pre-set dosing interval has elapsed. As soon as the dosing interval has elapsed, any demand signal generated by the operation of the trigger means by the patient will pass as an inject signal to the second timer to activate the motorized syringe 28 thus providing the required dosage to the patient.

From the foregoing it will be apparent that the attempt counter 16 monitors and records the total number of attempts which the patient makes to obtain a drug dosage and the inject counter 22 monitors and records the total number of injections which the patient has received.

I have found that by analyzing the output from the counters 16 and 22 as previously described, valuable information can be obtained.

The trigger mechanism may be in the form of a conventional switch mechanism such as a push button switch.

The counters 16 and 18 may be in the form of a conventional counter such as those manufactured by Hecon Co. Can. Inc. and sold under the Trade Name Hecon Series 404, Totalizer.

The timers 18 and 24 may be conventional timers such as those manufactured by G & W Eagle Signal, Industrial Division and sold under the Trade Name "Cycl-Flex" Reset Timers.

The motorized syringe may be in the form of a non-battery driven electric motor pump such as that manufactured by Extramedic Corporation and sold under the Trade Name Holter pump (modified).

What I claim as my invention is:

1. A device for monitoring and controlling the operation of a motorized syringe to dispense a predetermined drug dosage comprising;
   (a) trigger means operable by a patient to initiate a demand signal indicative of a demand for an individual drug dose,
   (b) first signal monitor means adapted to record the total number of occasions on which said demand signal is initiated by operation of said trigger means,
   (c) first timer means for receiving said demand signal and selectively rejecting said demand signal or emitting said demand signal as an inject signal,
   (d) second signal monitor means adapted to record the total number of occasions on which said first timer means emits a demand signal,
   (e) second timer means for receiving said inject signal, said second timer means being operable on receipt of said inject signal to activate said motorized syringe for a preselected timer period to dispense a predetermined individual dose of drug.

2. A device for monitoring and controlling self-administration of intravenous drug dosages comprising;
   (a) drug dispensing means operable to dispense a drug dosage to a patient,
   (b) trigger means operable by a patient to initiate a demand signal indicative of a patient's demand for a drug dosage,
   (c) first signal monitor means adapted to record the total number of occasions on which said demand signal is initiated by operation of said trigger means,
   (d) first timer means for receiving said demand signal and selectively rejecting said demand signal or emitting said demand signal as an inject signal,
   (e) second signal monitor means adapted to record the total number of occasions on which an inject signal is emitted by said first timer,
   (f) second timer means for receiving the inject signal, said second timer means being operable on receipt of an inject signal to activate said drug dispensing means for a preselected time period to dispense a predetermined individual dose of said drug.

* * * * *

REEXAMINATION CERTIFICATE (413th)
United States Patent [19]
Keeri-Szanto

[11] B1 4,275,727
[45] Certificate Issued Nov. 5, 1985

[54] DEVICE FOR MONITORING AND CONTROLLING SELF-ADMINISTERED INTRAVENOUS DRUG DOSAGE

[76] Inventor: Michael Keeri-Szanto, 10 Beechwood Pl., Apt. 612, London, Ont., Canada, N6C 1H7

Reexamination Request:
No. 90/000,379, May 10, 1983

Reexamination Certificate for:
Patent No.: 4,275,727
Issued: Jun. 30, 1981
Appl. No.: 109,928
Filed: Jan. 7, 1980

[51] Int. Cl.$^4$ .............................................. A61M 5/00
[52] U.S. Cl. .................................... 604/66; 604/246; 128/DIG. 13; 222/14
[58] Field of Search ................... 604/246, 65, 66, 67, 604/131; 222/14-22

[56] References Cited

PUBLICATIONS

Philip H. Sechzer, Studies in Pain With the Analgesic-Demand System, Anesthesia and Analgesia, Current Researches, vol. 50, No. 1, Jan.-Feb., 1971, pp. 1-10, (Appendix E).

William H. Forrest, Jr., Peter Smethurst, and Martin E. Kienitz, Self-Administered of Intravenous Analgesics, Clinical Workshop, Anesthesiology, Sep. 1970, vol. 33, No. 3, pp. 363-365, (Appendix F).

Michael Keeri-Szanto, Apparatus for Demand Analgesia, Canadian Anesthesiology Society Journal, vol. 18, No. 5, Sep. 1971, pp. 581-582, (Appendix G).

K. Chakravarty, W. Tucker, M. Rosen and M. D. Vickers, British Medical Journal, Oct. 13, 1979, vol. 2, pp. 895-897, (Appendix H).

Evans et al., Apparatus for Patient-Controlled Administration of Intravenous Narcotics During Labor, The Lancet, Jan. 3, 1976, (Appendix I).

Tamsen et al., Patient Controlled Analgesic Therapy in Postoperative Period, Tamsen et al., Acta. Anaesth. Scnd. 1979, 13, pp. 462-470, (Appendix J).

M. Keeri-Szanto, (Keeri-Szanto II), Drugs or Drums: What Relieves Postoperative Pain, M. Keeri-Szanto, M. D., Pain, 6, (1979), pp. 217-229, (Appendix K).

M. Keeri-Szanto (Keeri-Szanto III), Demand Analgesia For the Relief of Pain Problems In "Terminal" Illness, Anesthesiology Review, Feb. 1976, pp. 19-21, (Appendix L).

M. Keeri-Szanto et al. (Keeri-Szanto IV), Post Operative Demand Anathesia, Surgery, Gynecology and Obstetrics, Apr. 1972, vol. 134, pp. 647-651, (Appendix M).

M. Keeri-Szanto (Keeri-Szanto V), Demand Analgesia, Trends In Intravenous Anesthesia, 1980, pp. 417, 429, (Appendix N).

Primary Examiner—Stephen C. Pellegrino

[57] ABSTRACT

A device for monitoring and controlling the operation of a motorized syringe to dispense a predetermined drug dosage comprises, according to one aspect of this invention, a combination of a trigger, a first signal monitor, a first timer, a second signal monitor and a second timer. The trigger is operable by the patient to initiate a demand signal indicative of a demand for an individual drug dose. The first signal monitor serves to record the total number of occasions on which a demand signal is initiated by operation of the trigger. The first timer receives the demand signal and selectively rejects the demand signal or emits the demand signal as an inject signal. The second signal monitor records the total number of occasions on which the first timer emits a demand signal. The second timer receives the inject signal and is operable upon receipt of the inject signal to activate a motorized syringe for a preselected time period to dispense a predetermined individual dose of drug.

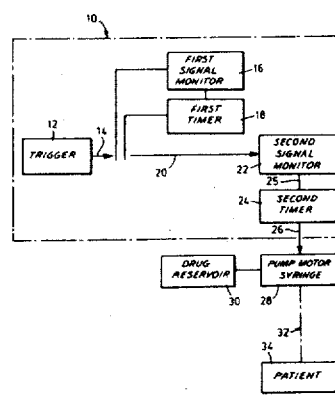

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1 and 2 are cancelled.

* * * * *